United States Patent [19]

Froesch et al.

[11] Patent Number: 4,988,675

[45] Date of Patent: Jan. 29, 1991

[54] METHOD FOR PREVENTING SECONDARY EFFECTS

[75] Inventors: Ernst R. Froesch, Erlenbach; Hans-Peter Guler, Adliswil; Christoph Schmid, Zurich; Jürgen Zapf, Zurich, all of Switzerland

[73] Assignee: Ciba-Geigy Corporation, Ardsley, N.Y.

[21] Appl. No.: 301,680

[22] Filed: Jan. 25, 1989

[30] Foreign Application Priority Data

Feb. 5, 1988 [CH] Switzerland ............... 810072/88

[51] Int. Cl.$^5$ ............... A61K 37/26; A61K 37/36
[52] U.S. Cl. ............... 514/4; 514/12
[58] Field of Search ............... 514/4, 12

[56] References Cited

FOREIGN PATENT DOCUMENTS 123228 10/1984 European Pat. Off. .

OTHER PUBLICATIONS

Scheiwiller et al., Nature, vol. 323, 11, Sep. 1986, pp. 169–171.
Stedman, Stedman's Medical Dictionary, p. 880, 24th Edition, 1982, Williams & Wilkins.
Guler et al., New England Journal of Medicine, vol. 317, No. 3, pp. 137–140, (1987).

*Primary Examiner*—Howard E. Schain
*Assistant Examiner*—Choon Koh
*Attorney, Agent, or Firm*—Henry P. Nowak; Irving M. Fishman; JoAnn Villamizar

[57] ABSTRACT

The invention concerns a method for treating and preventing secondary effects of hyperinsulinemia by application of insulin-like growth factor I (IGF I), and pharmaceutical compositions comprising IGF I which are useful for this purpose.

10 Claims, 3 Drawing Sheets

METHOD FOR PREVENTING SECONDARY EFFECTS

FIELD OF THE INVENTION

The invention concerns a method for treating and preventing secondary effects of hyperinsulinemia by application of insulin-like growth factor I (IGF I), and pharmaceutical compositions comprising IGF I which are useful for this purpose.

BACKGROUND OF THE INVENTION

Insulin regulates blood glucose by
(a) decreasing glucose outflow from the liver and
(b) increasing glucose uptake in peripheral tissues, e.g. muscles and adipose tissues.

Insulin exerts these effects by interacting with the insulin receptor present on most cells. The sensitivity to insulin is a function of the number of insulin receptors of individual cells. This number is decreased or "down-regulated" by insulin, i.e. high concentrations of insulin secondarily lead to relative insulin resistance. Conditions characterized by an excessive endogenous insulin secretion are obesity, type 2 diabetes, hyperlipidemia type IV of Fredricksen. In type 1 diabetes (juvenile diabetes mellitus, insulin dependent) insulin resistance is the consequence of the peripheral administration of insulin so that the glucose homeostatic function of the liver is impaired and peripheral glucose uptake excessive. The treatment of obesity, type 2 diabetes (non-insulin dependent) and hyperlipidemia consists primarily of dietary measures, i.e. caloric restriction. Patient compliance is notoriously bad and there is a need for new and better therapeutic measures. In insulin treated type 1 diabetes, hyperinsulinemia results from the fact that insulin is delivered s.c. rather than intraportally so that the delivered insulin reaches peripheral tissues first rather than after passage through the liver. There is a need to overcome the drawbacks of excessive insulin secretion and hyperinsulinemia.

Insulin-like growth factor I (IGF I) has been shown to lower blood glucose in man after intravenous bolus injection (1). Growth-promoting actions of IGF I have been documented in several metabolic conditions which have low IGF I levels in common, e.g. hypophysectomized rats (2) (5), diabetic rats (3) and Snell dwarf mice (4).

It has now been found that prolonged infusions of IGF I inhibit growth hormone secretion. In addition, blood glucose and peripheral levels of insulin remained constant but the levels of the C-peptide fell markedly indicating that endogenous insulin secretion was reduced. During IGF I infusion triglyceride, cholesterol and LDL-cholesterol tended to decrease while HDL-cholesterol increased. These findings show that during IGF I infusions insulin secretion is decreased and that IGF I helps to maintain glucose homeostasis with considerably less insulin thus overcoming the drawbacks of hyperinsulinemia. There are at least two mechanisms of action of IGF 1: As shown in the bolus experiments, IGF I leads to hypoglycemia by increasing glucose uptake primarily of muscle. It is conceivable that IGF I infusions may also facilitate glucose uptake by muscle and this effect is dose related. The second, so far unknown effect has to do with insulin degradation.

So far there exists no report on the inhibition of insulin secretion during administration of IGF I. It is foreseen that the administration of IGF I leads to a diminished need of insulin thereby preventing the secondary effects of hyperinsulinemia.

OBJECT OF THE INVENTION

Object of the invention is to prevent the secondary effects of administered insulin in diabetics and to minimize the effets of excessive endogenous insulin in obesity, typ 2 diabetes and hyperlipidemia.

Further object of the invention is to provide pharmaceutical compositions containing IGF I in dosage unit form and in such amounts as to achieve said beneficial effects.

DETAILED DESCRIPTION

Figure 1:
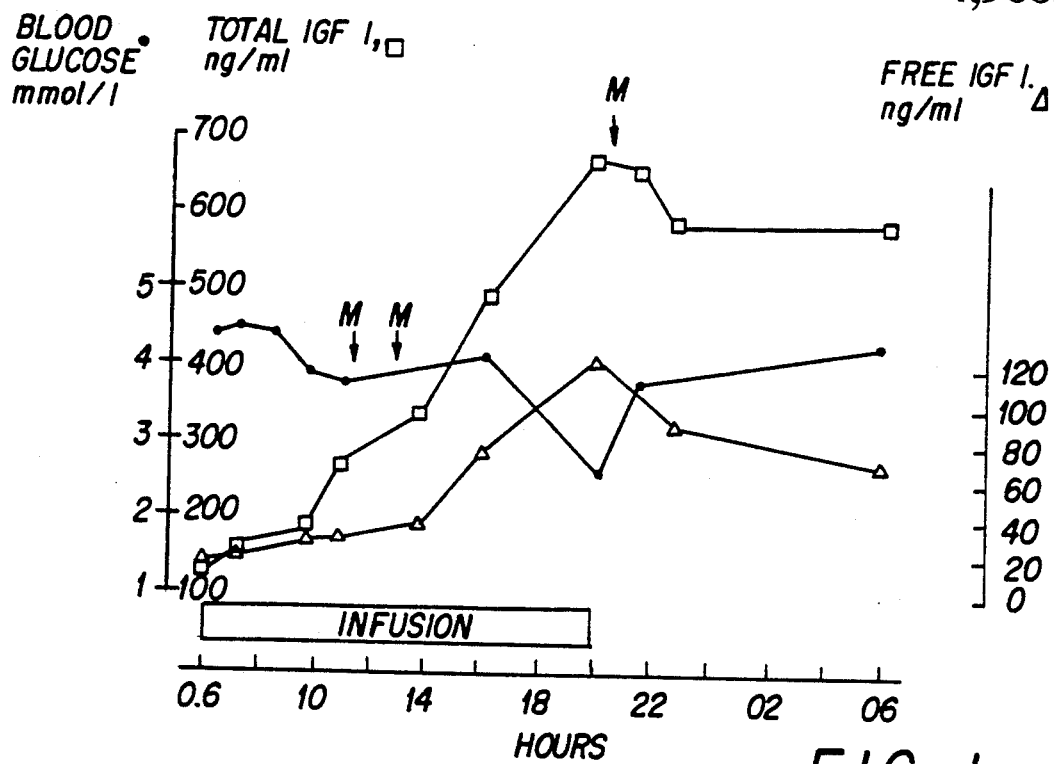

The invention concerns a method for treating and preventing secondary effects of hyperinsulinemia in diabetics treated with insulin, characterized in that an effective amount of IGF I and a lower than normal amount of insulin is administered.

The invention also concerns a method for treating type 2 diabetics, obese subjects and subjects with hyperlipidemia characterized in that an effective amount of IGF I alone is administered.

Any source of IGF I can be used whether from natural sources or synthetically produced. Preferred is recombinant human IGF I (rhIGF I), prepared e.g. according to EP 123 228.

Any type of insulin may be used, such as from pork or bovine, or preferably human recombinant insulin.

An effective amount is defined as an amount having a therapeutic effect on the envisioned conditions to be treated.

IGF I is administered intravenously, subcutaneously or intramuscularly in doses between about 24 $\mu$g/kg/day up to about 720 $\mu$g/kg/day, or if given continuously in doses of about 1 $\mu$g/kg/h up to about 30 $\mu$g/kg/h, either by two daily injections or by subcutaneous infusions, e.g. via a minipump, respectively. During 6 days a total of about 3000 $\mu$g/kg equivalent to a total daily dose of 500 $\mu$g/kg may be administered.

If IGF I is administered together with insulin the latter is used in lower amounts than if used alone, down to amounts which by themselves have little effect on blood glucose, i.e. in amounts of between about 0.1 IU/kg/24 h up to about 0.5 IU/kg/24 h.

The dosage has of course to be adjusted to the patient's specific disease, the route of administration, the individual weight and general condition of the patient to be treated and is finally dependent on the judgement of the physician. Caution should be taken that blood glucose is monitored and hypoglycemia prevented.

Pharmaceutical compositions for preventing secondary effects in diabetics comprise an effective amount of IGF I, i.e. an amount of from about 20 mg to about 300 mg.

Due to the synergistic effects of the combination of IGF I and insulin, the latter is present in such combination in an amount of from 0.2 mg up to 10.0 mg.

In general the pharmaceutical preparation contains an effective amount of the active ingredient(s) together or in admixture with inorganic or organic, solid or liquid, pharmaceutically acceptable carriers which are suitable preferably for parenteral administration.

The active compound of the present invention, alone or in combination with insulin, is preferably used in the form of pharmaceutical preparations such as infusion solutions for parenteral, for example subcutaneous, intramuscular or intravenous, administration. Such solutions are preferably isotonic aqueous solutions or suspensions which can be prepared before use, for example from lyophilised preparations which contain the active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations, which may, if desired, contain further pharmacologically valuable substances, are produced in a manner known per se, for example by means of conventional dissolving or lyophilising processes, and contain from approximately 0.1% to 100%, especially from approximately 1% to approximately 50%, and in the case of lyophilisates up to 100%, of the active ingredient(s).

If a combination of IGF I and insulin is envisaged, it can be in a fixed form, i.e. predetermined amounts of both active ingredients are combined in one dosage unit form, or in separated dosage unit forms. The latter form allows to adjust the dose for each compound more individually.

The invention concerns also a synergistic antidiabetic pharmaceutical combination of IGF I and insulin, and a method for the manufacture of a pharmaceutical preparation for treating and preventing secondary effects of hyperinsulinemia in diabetics treated with insulin, characterized in that IGF I and a lower than normal amount of insulin are pharmaceutically processed according to conventional methods.

The invention concerns further the use of the pharmaceutical combinations for the prevention of secondary effects of hyperinsulinemia in diabetics treated with insulin.

The invention concerns further a method for the manufacture of a pharmaceutical preparation for treating type 2 diabetics, obese subjects or subjects with hyperlipidemia, characterized in that IGF I is pharmaceutically processed according to conventional methods.

The invention concerns also the use of IGF I alone for the manufacture of a pharmaceutical preparation for the prevention of secondary effects in type 2 diabetics, obese subjects and subjects with hyperlipidemia which may contain instructions for its use, and the use of IGF I for the manufacture of a synergistic combination comprising IGF I and insulin.

The invention concerns also a pharmaceutical preparation or pack comprising IGF I or a combination of IGI and insulin, and which may include instructions for use.

Following are examples of pharmaceutical preparations according to the invention which, however, should not be construed as a limitation thereof. In the Examples the term IGF I, it not otherwise specified, relates to recombinant human IGF I (rhIGF I), which was prepared according to EP 123 228. It has been characterized chemically and biologically and found to be identical to highly purified extracted human IGF I. The same material had been used in a previous study in man (1).

1. Example for a Pharmaceutical Preparation with IGF I Alone

Dry ampoules containing 50 mg or 300 mg of IGF I: ampoules of 5 ml or 50 ml, respectively, volume are filled with 5 ml or 30 ml, respectively, of sterile filtered 10% (w/v) aqueous solution of IGF I and lyophilized. The infusion solution is prepared by adding the respective volume (5 or 30 ml) of sterile water, physiological saline, or 0.1 M acetic acid.

The therapeutic combination contains the desired number of ampoules necessary for one course of treatment, e.g. for 6 days, and optional instructions for application which stipulate the time during which the medicament should be infused.

2. Example for a Pharmaceutical Preparation with IGF I and Insulin

Dry ampoules containing 50 mg or 300 mg of IGF I: ampoules of 5 ml or 50 ml, respectively, volume are filled with 5 ml or 30 ml, respectively, of sterile filtered 10% (w/v) aqueous solution of IGF I. Insulin, preferably human recombinant insulin, is added in an amount of 0.2 mg or 10 mg, and the vials are lyophilized. The infusion solution is prepared by adding the respective volume (5 or 30 ml) of sterile water, physiological saline, or 0.1 M acetic acid.

The therapeutic combination contains the desired number of ampoules necessary for one course of treatment, e.g. for 6 days, and optional instructions for application which stipulate the time during which the medicament should be infused.

1. Example for Treatment of Humans

Subjects

Two males (age/body weight/height):1.:38/65/172; 2.:34/61/1.72) served as normal subjects in this clinical trial. Their body weight was ideal and they had no clinical evidence of illness and did not take any medication. Routine hematology, blood chemistry and endocrine parameters were within normal limits.

Experimental Protocol

Baseline values were obtained during an initial control period after which IGF I was administered by continuous s.c.infusion during six days. This method and duration of administration was selected in order to reach constant serum levels of IGF I. The study was concluded with a second control period. Food intake was strictly controlled during the whole study and consisted of 2500 kcal per day (25% protein, i.e. 1.9 g protein per kilogram body weight, 20% fat and 55% carbohydrate).

Subject 1:Both control periods lasted for three days. On the first day of treatment, IGF I was initially infused at an arbitrary dose of 32.0 µg per kilogram body weight and hour. This dose of IGF I caused hypoglycemia (see result section). 20.0 µg per kilogram body weight and hour during the next five days were found to be safe and blood glucose remained normal. The total amount of IGF I infused during six days was 184 mg.

Subject 2:Both control periods were five days. IGF I was infused at the same dose as in subject 1 (20.0 µg per kilogram body weight and hour) during a total of six days. The total amount of IGF I infused was 167 mg.

Infusion Device:A miniaturized insulin-infusion device (MRS 1 Infusor[R]/Disetronic AG, Burgdorf, Switzerland) was used. IGF I was dissolved in 0.1 M acetic acid. 25 pl per hour were infused. The infusor cartridge containing the IGF I was refilled after 3 days. A microcatheter was placed under the skin of the abdomen. It was changed after 3 days and placed at a location distant from the first one.

Serum levels of insulin and C-peptide were measured every morning in fasting serum samples and in subject 2 also during the sixth night of IGF I infusion as well as during a night several weeks after the infusion.

Venous Blood was obtained every morning between 6 and 7 a.m. It was immediately placed on ice and centrifuged one hour later. Serum or plasma was stored in 1 ml portions at $-20°$ C. All assays were done in samples that had not been thawed before.

24 Hours-Urine collections were obtained throughout the study (6 a.m. to 6 a.m.). Several aliquots were stored at $-20°$ C.

Assays

Total IGF I and free IGF I were measured by radioimmunoassay as described earlier (6, 7). Blood glucose was determined by YSI 23A glucose analyzer. Commercially available kits were used to determine growth hormone (hGH-RIA-Kit, Medipro, Teufen, Switzerland), insulin (RIA-GNOST Insulin, Behringwerke AG, Marburg, Germany) and C-peptide (RIA kit for human C-peptide, Medigenix, Fleurus, Belgium). All other analyses were kindly performed in the Department of Clinical Chemistry of the University Hospital of Zurich.

Results

IGF-I Dose finding in subject 1 (FIG. 1)

After three control days (without any hormone) the IGF I infusion was started at 6.30 a.m. at a rate of 32.0 $\mu$g per kilogram body weight per hour. Blood glucose was 4.4 mmol per liter, the serum level of total IGF I 120 ng per milliliter and that of free IGF I 20 ng per milliliter. 13.5 hours later, after the infusion of a total of 28.1 mg of IGF I and 8 hours after the last meal, blood glucose had fallen to 2.6 mmol per liter without any clinical signs of hypoglycemia. By that time the serum level of total IGF I had reached 683 ng per milliliter, and the serum level of free IGF I was 123 ng per milliliter. The infusion was stopped overnight and started again on the next morning at 6.30 a.m. at a rate of 20.0 $\mu$g per kilogram body weight and hour. This dose was kept constant during the subsequent 5 days in subject 1 and was also used during the whole six day infusion period in subject 2.

Clinical Observations

Apart from the hypoglycemic episode in subject 1 on the first day of the IGF I infusion, no other such event was recorded. Both subjects felt normal throughout the study. Blood pressure, pulse rate, body temperature and body weight remained stable.

Blood Glucose

Blood glucose was monitored daily after overnight fasting (at least 12 hours) and remained between 3.7 to 4.4 mmol per liter throughout the study. In subject 2 blood glucose levels measured every hour during one night of IGF I infusion were between 3.6 and 4.4 mmol per liter.

Serum Levels of Triglycerides

Serum levels of triglycerides of subject 2 were determined by a routine enzymatic colour test (GPO-PAP) with an Hitachi 737 Multi Analyser of blood samples drawn in the morning after an over-night fast.

In a similar manner three further subjects were treated with 20 $\mu$g/kg/h of IGF I and the serum levels of triglycerides determined.

The results are compiled in Table 1.

TABLE 1

| Day | Triglyceride Level in mmol/l | | | |
|---|---|---|---|---|
| | Subject 2 | Subject 3 | Subject 4 | Subject 5 |
| −3 | 1.65 | 1.59 | 0.70 | — |
| −2 | 1.37 | — | — | — |
| −1 | 1.24 | 1.54 | 0.76 | 1.24 |
| 1 | 1.50 | 0.98 | 0.75 | 1.29 |
| 2@ | 1.12 | 1.01 | 0.54 | 0.61 |
| 3@ | 0.77 | 0.63 | 0.63 | 0.92 |
| 4@ | 0.78 | 0.99 | 0.51 | 0.81 |
| 5@ | 0.74 | 0.69 | 0.60 | 0.48 |
| 6@ | 0.74 | 0.73 | 0.69 | 0.70 |
| 7 | 1.06 | 1.23 | 0.52 | 0.85 |
| 8 | 1.16 | 1.21 | 0.70 | 0.79 |
| 9 | 1.24 | 0.93 | 0.57 | 0.72 |
| 11 | 1.93 | 1.31 | 0.58 | 0.66 |

Figure 2A:
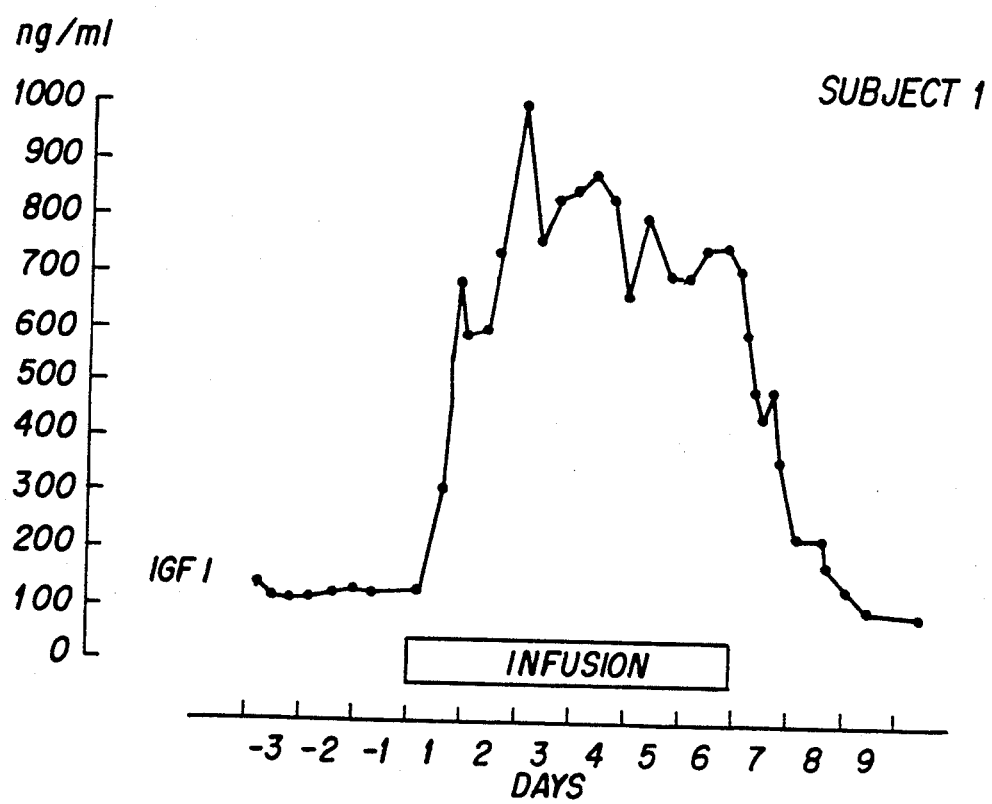
Figure 2B:
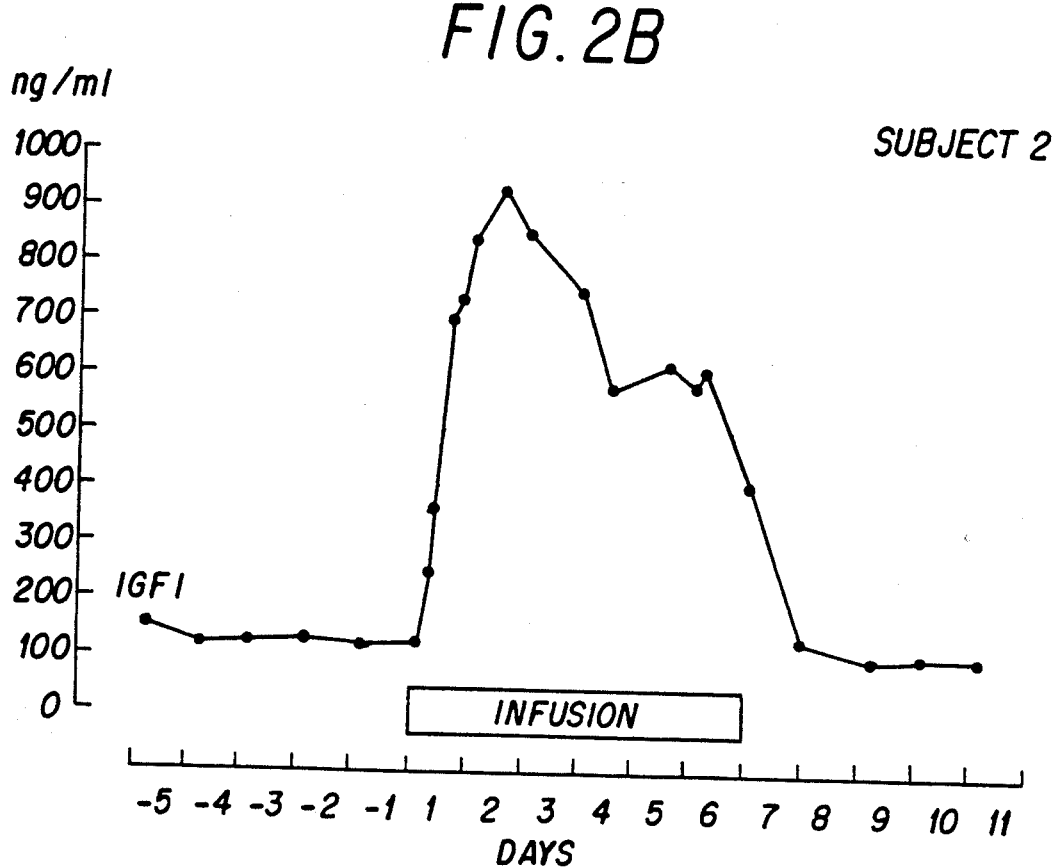

Serum Levels of Total IGF I (FIG. 2)

Within two to four hours after starting the infusion, IGF I levels rose and reached levels of 700 ng per milliliter after 13 to 14 hours. Peak levels in the two subjects were 980 and 920 ng per milliliter, respectively. When the infusion was stopped IGF I levels fell in the normal range within one day.

Serum Levels of Free IGF I

Free IGF I levels during the control days were between 15 and 20 ng per milliliter and between 50 and 80 ng per milliliter during continuous IGF I infusion.

Figure 3A:
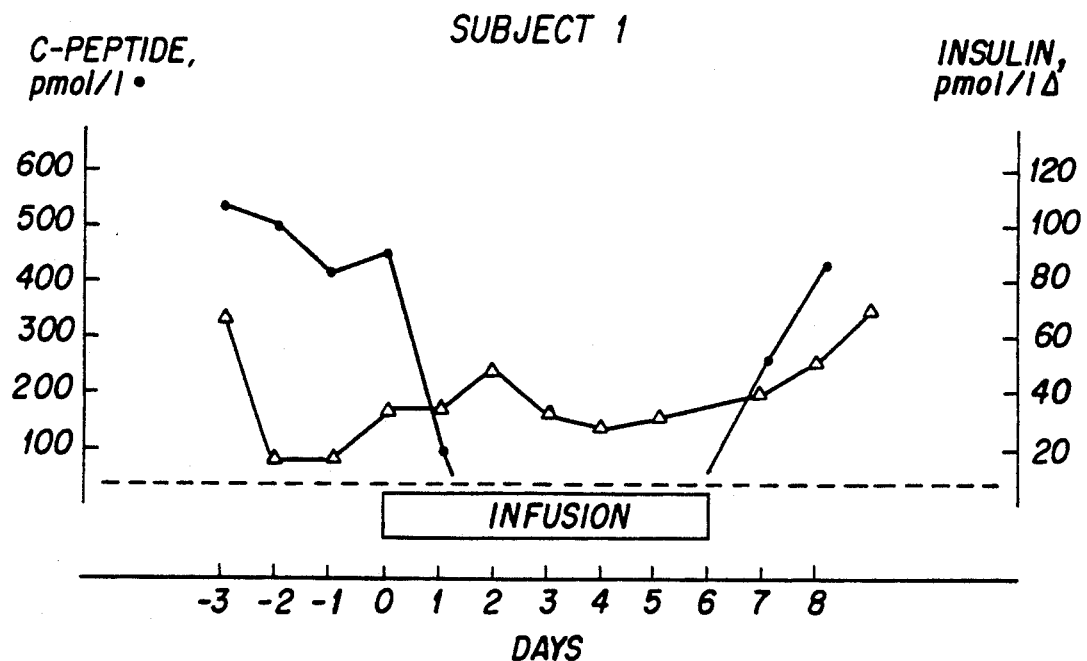
Figure 3B:
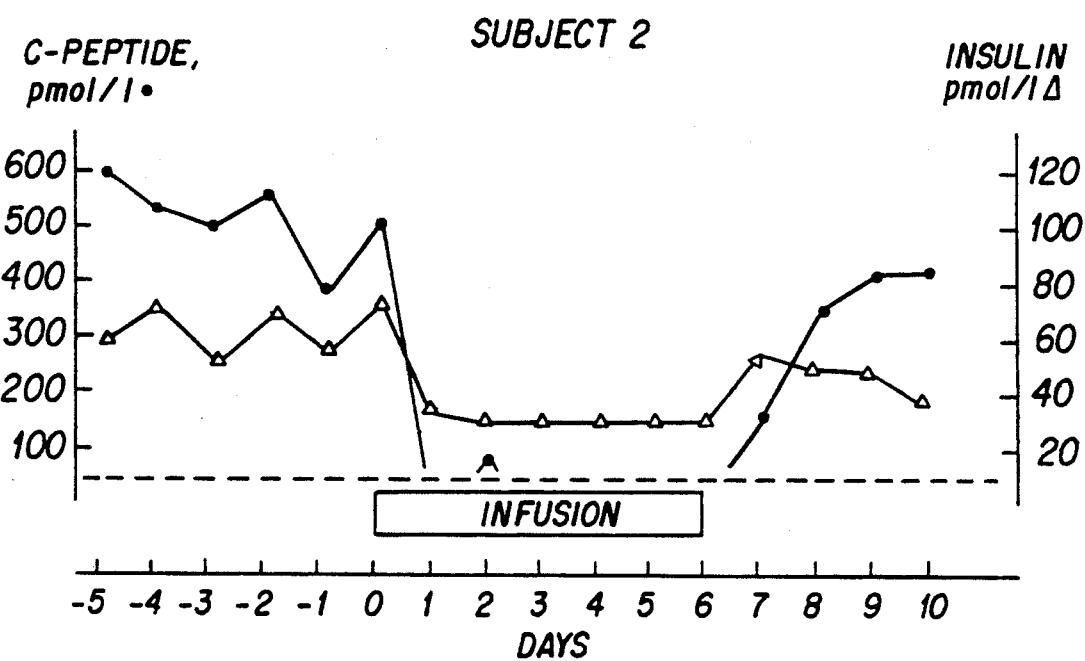

Fasting Serum Levels of Insulin (FIG. 3)

All fasting insulin values before, during and after the infusion were between 17 and 77 pmol per liter. Similar values were found in subject 2 during the sixth night and five weeks after the infusion in blood samples taken every hour (51 to 77 pmol per liter).

Serum levels of C-peptide (FIG. 3, 4)

Figure 4:
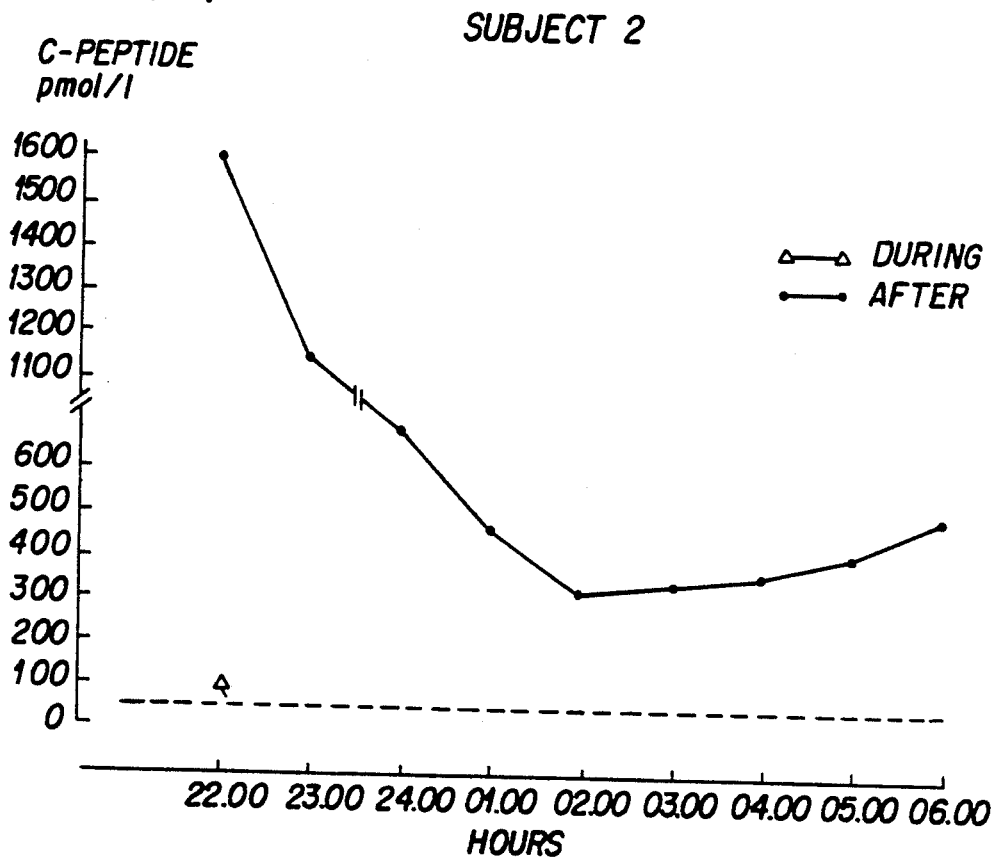

Fasting serum levels of C-peptide drawn every morning before and after the infusion were 450±80 pmol per liter, whereas during the infusion period all but two values (95 and 69 pmol per liter, respectively) were below the detection limit of the assay (50 pmol per liter) (FIG. 3). Serum levels of C-peptide were also measured during the sixth night of the infusion in subject 2: all but one value at 10 p.m. (98 pmol per liter) were below 50 pmol per liter. During a control night five weeks after the infusion C-peptide levels were 650±440 pmol per liter (FIG. 4).

Discussion of the Results

Subcutaneous infusions of IGF I in a dose of 20.0 $\mu$g per kilogram body weight and hour to healthy adults are safe, do not influence general well-being, blood pressure, pulse rate and body temperature and do not lead to hypoglycemia. Under the IGF I infusion serum levels of triglyceride are markedly reduced. Morning fasting serum levels of insulin remain in the normal range whereas C-peptide levels are below 50 pmol/l (FIG. 3).

Normal insulin levels in the presence of decreased C-peptide levels, as observed in the present study, indicates a decrease of insulin degradation and consecutively a prolongation of its half-life.

IGF I appears to make the organism more sensitive to insulin and from this point of view becomes a potentially very exciting therapeutic tool for the treatment of insulin resistance, such as in type 2 diabetes, obesity, hyperlipidemia, and, of course, also type 1 diabetes.

Legend to Figures

FIG. 1: Blood glucose and free IGF I serum levels on the first day of continuous s.c. infusion of recombinant IGF I at a rate of 32.0 μg per kilogram body weight and hour in subject 1. The infusion was begun at 6.30 a.m. and stopped at 8.00 p.m. when blood glucose had fallen to 2.6 mmol per liter. Serum levels of free IGF I by that time had increased from basel values of 20 ng per milliliter to 123 ng per milliliter. "M" indicates the time of the meals.

FIG. 2: Serum levels of total IGF I in two subjects before, during and after six days under constant s.c. infusion of recombinant IGF I in a dose of 20.0 μg per kilogram body weight and hour.

FIG. 3: Serum levels of C-peptide and insulin in two subjects before, during and after six days under constant s.c. infusion of recombinant IGF I in a dose of 20 μg per kilogram body weight per hour. The dotted line represents the detection limit of the assay.

FIG. 4: C-peptide levels in subject 2 from 10 p.m. to 6 a.m. during the sixth night of IGF I infusion (A) and during a control night (.) five weeks later. Blood glucose and insulin were within normal limits on both occasions. The dotted line represents the detection limit of the assay.

References

1. Guler HP, Zapf J, Froesch ER. Short-term metabolic effects of recombinant human insulin-like growth factor I in healthy adults. N Engl J Med 1987; 317:137-40.

2. Guler HP, Zenobi P, Zapf J, et al. IGF I and II and recombinant human IGF I are hypoglycemic in the rat, mini-pig, and men. Endocrinology 1986; 118:Suppl:129, abstract.

3. Scheiwiller E, Guler HP, Merryweather J, Scandella C, Maerki W, Zapf J, Froesch ER. Growth restoration of insulin-deficient diabetic rats by recombinant human insulin-like growth factor I. Nature 1986; 323:169-71.

4. van Buul-Offers S, Ueda I, Van den Brandle JL. Biosynthetic somatomedin C (SM-C/IGF-I) increases the length and weight of Snell dwarf mice. Pediatr Res 1986; 20:825-7.

5. Guler HP, Zapf J, Froesch ER. S.c. infusion of recombinant human insulin-like growth factor I (rhIGF I) stimulates growth of hypophysectomized rats continuously during 18 days. Proceedings of the 1st European Congress of Endocrinology, Copenhagen 1987; 103, abstract 12-390.

6. Zapf J, Walter H, Froesch ER. Radioimmunological determination of insulin-like growth factors I and II in normal subjects and in patients with growth disorders and extrapancreatic tumor hypoglycemia. J Clin Invest 1981; 68:1321-30.

7. Zapf J, Hauri C, Waldvogel M, Froesch ER. Acute metabolic effects and half-lives of intravenously administered insulin-like growth factors I and II in normal and hypophysectomized rats. J. Clin Invest 1986; 77:1768-75.

We claim:

1. A method for treating and preventing secondary effects of hyperinsulinemia in diabetics treated with insulin, characterized in that an effective amount of IGF I and a lower than normal amount of insulin is administered.

2. A method for treating type 2 diabetics, obese subjects or subjects with hyperlipidemia, characterized in that an effective amount of IGF I alone is administered.

3. A method according to claim 1, characterized in that recombinant IGF I is used.

4. A method according to claim 1, characterized in that IGF I is administered in an amount of from about 24 μg/kg/day up to about 720 μg/kg/day.

5. A method according to claim 1, characterized in that in addition to IGF I insulin is administered in lower amounts than if used alone.

6. A method according to claim 1, characterized in that in addition to IGF I insulin is administered in amounts which by themselves have little effect on blood glucose.

7. A method according to claim 1, characterized in that in addition to IGF I insulin is administered in amounts of between 0.2 IU/kg/24 h up to about 0.5 IU/kg/24 h.

8. A method according to claim 1, characterized in that IGF I is subcutaneously or intravenously infused via a minipump.

9. A method according to claim 1, characterized in that IGF I is subcutaneously, intravenously or intramuscularly administered continuously in a dose of about 1 μg/kg/h up to about 24 μg/kg/h.

10. Method for the manufacture of a pharmaceutical preparation for treating and preventing secondary effects of hyperinsulinemia in diabetics treated with insulin characterized in that IGF I and a lower than normal amount of insulin are pharmaceutically processed.

* * * * *